US011224401B2

(12) United States Patent
Ogura et al.

(10) Patent No.: US 11,224,401 B2
(45) Date of Patent: Jan. 18, 2022

(54) ULTRASONIC MEASUREMENT METHOD, ULTRASONIC MEASUREMENT APPARATUS, AND PROGRAM STORAGE DEVICE READABLE BY MACHINE

(71) Applicants: SHISEIDO COMPANY, LTD., Tokyo (JP); NATIONAL UNIVERSITY CORPORATION TOYOHASHI UNIVERSITY OF TECHNOLOGY, Aichi (JP); HONDA ELECTRONICS CO., LTD., Aichi (JP)

(72) Inventors: Yuki Ogura, Tokyo (JP); Naohiro Hozumi, Aichi (JP); Sachiko Yoshida, Aichi (JP); Kazuto Kobayashi, Aichi (JP); Yusuke Hara, Tokyo (JP)

(73) Assignees: SHISEIDO COMPANY, LTD., Tokyo (JP); NATIONAL UNIVERSITY CORPORATION TOYOHASHI UNIVERSITY OF TECHNOLOGY, Aichi (JP); HONDA ELECTRONICS CO., LTD., Aichi (JP)

( * ) Notice: Subject to any disclaimer, the term of this patent is extended or adjusted under 35 U.S.C. 154(b) by 115 days.

(21) Appl. No.: 16/841,812

(22) Filed: Apr. 7, 2020

(65) Prior Publication Data

US 2020/0330069 A1    Oct. 22, 2020

(30) Foreign Application Priority Data

Apr. 17, 2019 (JP) .............................. JP2019-078727

(51) Int. Cl.
*A61B 8/08* (2006.01)
*G01B 17/02* (2006.01)
*A61B 8/00* (2006.01)

(52) U.S. Cl.
CPC ............ *A61B 8/0858* (2013.01); *A61B 8/461* (2013.01); *A61B 8/485* (2013.01); *G01B 17/02* (2013.01)

(58) Field of Classification Search
CPC ....... A61B 8/0858; A61B 8/461; A61B 8/485; A61B 8/4281; A61B 8/5223; A61B 8/54; G01B 17/02; G01B 17/025
See application file for complete search history.

(56) References Cited

U.S. PATENT DOCUMENTS

| 4,145,917 A * | 3/1979 | Brazhnikov | G01N 29/032 |
| | | | 73/64.53 |
| 6,575,043 B1 * | 6/2003 | Huang | G01F 1/002 |
| | | | 73/861.18 |

FOREIGN PATENT DOCUMENTS

| EP | 0335808 A1 * | 10/1989 | ............. G01N 29/07 |
| JP | 4654352 | 3/2011 | |

(Continued)

OTHER PUBLICATIONS

Egawa, et al., British Journal of Dermatology, "Comparison of the depth profiles of water and water-binding substances in the stratum corneum determined in vivo by Raman spectroscopy between the cheek and volar forearm skin: effects of age, seasonal changes and artificial forced hydration", 2008, 158, 251-260.

(Continued)

*Primary Examiner* — Bo Joseph Peng
(74) *Attorney, Agent, or Firm* — IPUSA, PLLC

(57) ABSTRACT

An ultrasonic measurement method includes irradiating an object to be measured with an ultrasonic wave, acquiring a reflection wave from the object, calculating at a processor an acoustic impedance in a depth direction of the object from the reflection wave, and estimating and outputting a thick- (Continued)

ness of the object based upon an inflection point determined by second-order differentiation of the acoustic impedance.

11 Claims, 13 Drawing Sheets

(56) References Cited

FOREIGN PATENT DOCUMENTS

| | | | |
|---|---|---|---|
| JP | 6361001 | 7/2018 | |
| SU | 1979-06157 B | * 4/1978 | ............. G01B 17/02 |
| WO | 2018207276 | 11/2018 | |

OTHER PUBLICATIONS

E. Boireau-Adamezyk et al., Skin Research and Technology, "Age-dependent changes in stratum corneum barrier function", 2014, 20, 409-415.

* cited by examiner

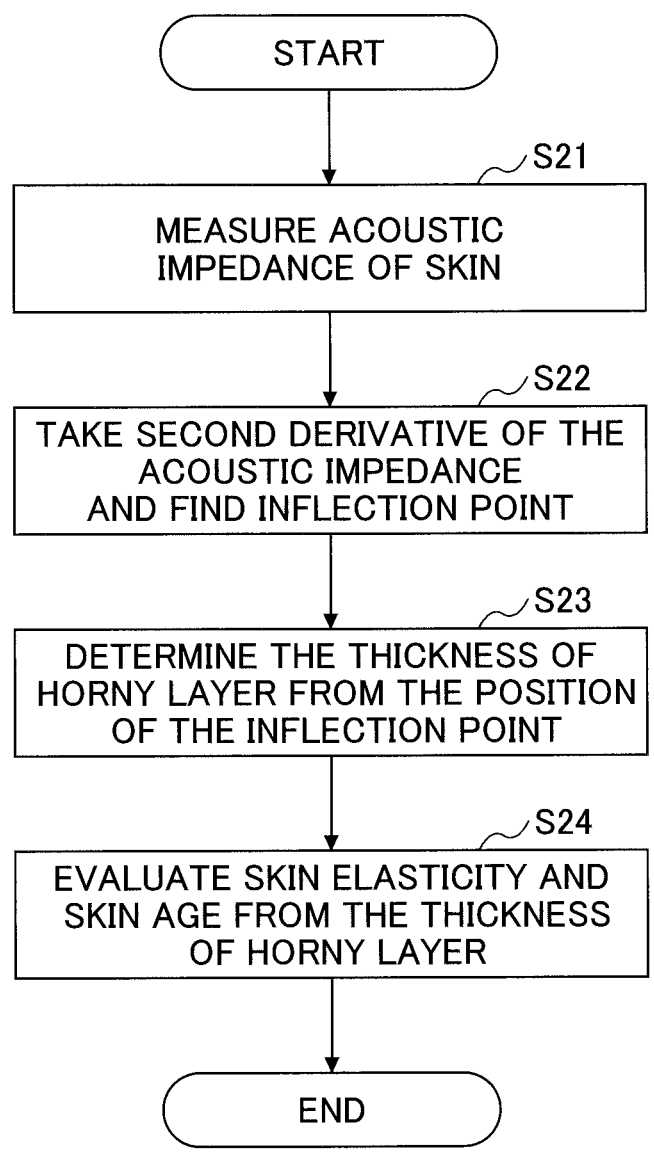

ULTRASONIC MEASUREMENT METHOD, ULTRASONIC MEASUREMENT APPARATUS, AND PROGRAM STORAGE DEVICE READABLE BY MACHINE

CROSS REFERENCE

This application is based upon and claims priority to earlier filed Japanese Patent Application No. 2019-078727 filed Apr. 17, 2019, which is incorporated herein by reference in its entirety.

TECHNICAL FIELD

The present invention relates to an ultrasonic measurement method, an ultrasonic measurement apparatus, and a program storage device readable by a machine.

BACKGROUND ART

Evaluation of surface characteristics of an object is useful in various fields. As for a living body, skin exists on the exterior surface of the body. By understanding skin type or condition, which are characteristics of skin, a skincare regime that is suitable for the skin type or condition can be chosen, in order to maintain healthy skin. In the fields of beauty and cosmetics, in addition to evaluating skin condition through interviews with beauty technicians, objective evaluation of skin conditions and functions is also performed using measuring equipment to determine mechanical properties such as skin flexibility and elasticity, as well as optical properties such as skin luster and transparency.

With a conventional elasticity measuring scheme that applies stress from the skin surface to cause deformation, the stress reaches the dermis and subcutaneous tissue located deeper than the epidermis, and a whole characteristic value including all of the contributions from the layers constituting the skin (i.e., the horny layer, epidermis, dermis, and subcutaneous tissue).

Since each layer of the skin has its own role and function, it is desirable to measure and evaluate individual layers of the skin. In particular, the horny layer, the outermost layer of the skin, has barrier and moisturizing functions needed for maintaining vital activities. Accurate measurement of the characteristic values of the horny layer is an important issue in the medical and pharmaceutical fields. Besides, since the efficacy claims for skincare products are limited to the horny layer in terms of pharmaceutical regulations, characteristic evaluation of the horny layer only is meaningful in the beauty and cosmetic fields.

One of known techniques for identifying the horny layer is a Raman confocal microscope. (See, for example, Non-Patent Document 1 presented below). A specific molecule can be identified by Raman spectroscopy for analyzing the Raman spectrum unique to the substance. By identifying water molecules and acquiring the water distribution profile ranging from the skin surface to inside the skin, the horny layer can be distinguished from the living cells. In the detection using the water distribution profile, an aging change, namely, stratification of the horny layer due to aging is observed in the skin of a limb such as an arm (See, for example, Non-Patent Document 2 presented below.) With respect to the above, age-related changes in a face. Of which the horny layer is thinner than that of the limb, has not been observed so far.

In recent years, a technique of specifying an interface in the depth direction of skin using ultrasonic waves to determine a thickness of an individual layer is proposed. (See, for example, Patent Document 1 presented below). A method of constructing an ultrasonic tomographic image of a very thin object of a layered structure is also known. (See, for example, Patent Document 2 presented below).

In the cosmetic industry, ultrasonic measurement of inside of the skin is conducted generally for "measurement of the thickness of the entire skin layers" or "comparison of reflection intensities" using morphological information obtained from a reflection image. However, the reflection image of the ultrasonic wave represents superposition of reflected images from the interfaces of the layers having different acoustic impedances. For this reason, ultrasonic measurement using reflection images provides only rough information about the skin layer of the measured body part. Such information is insufficient to specify the position of individual layer or specify which layer strengthens the reflection. Especially, skin structure is complicated, unlike a simple lamination of plastics. Inside structure of a skin layer is different from a simple single structure; rather, there are multiple small interfaces existing in the layer and the reflection waveform from the interface of the layer is unclear. Among the skin layers, it is particularly difficult to accurately specify the position or thickness of a very thin horny layer.

PRIOR ART DOCUMENTS

Patent Document 1: Japan Patent No. 4654352
Patent Document 2: Japan Patent No. 6361001
Non-patent Document 1: Egawa, et al., British Journal of Dermatology 2008, 158, 251-260
Non-patent Document 2: E. Boireau-Adamezyk et al., Skin Research and Technology 2014, 20, 409-415

SUMMARY

One of the objectives of the present disclosure is to provide an ultrasonic measurement technique that enables to specify the position or the thickness of an interface of a target layer of an object to be measured from a layered structure of a plurality of thin layers.

To achieve the objective, second derivative analysis is employed focusing on a change in the acoustic impedance profile acquired from the measured object.

In one aspect of the disclosure, an ultrasonic measurement method includes irradiating an object to be measured with an ultrasonic wave, acquiring a reflection wave from the object, calculating at a processor an acoustic impedance in a depth direction of the object from the reflection wave, and estimating and outputting a thickness of the object based upon an inflection point determined by second-order differentiation of the acoustic impedance.

BRIEF DESCRIPTION OF THE DRAWINGS

FIG. 14 is a flowchart of a skin evaluation method using ultrasonic measurement.

DESCRIPTION OF EMBODIMENTS

Figure 1:
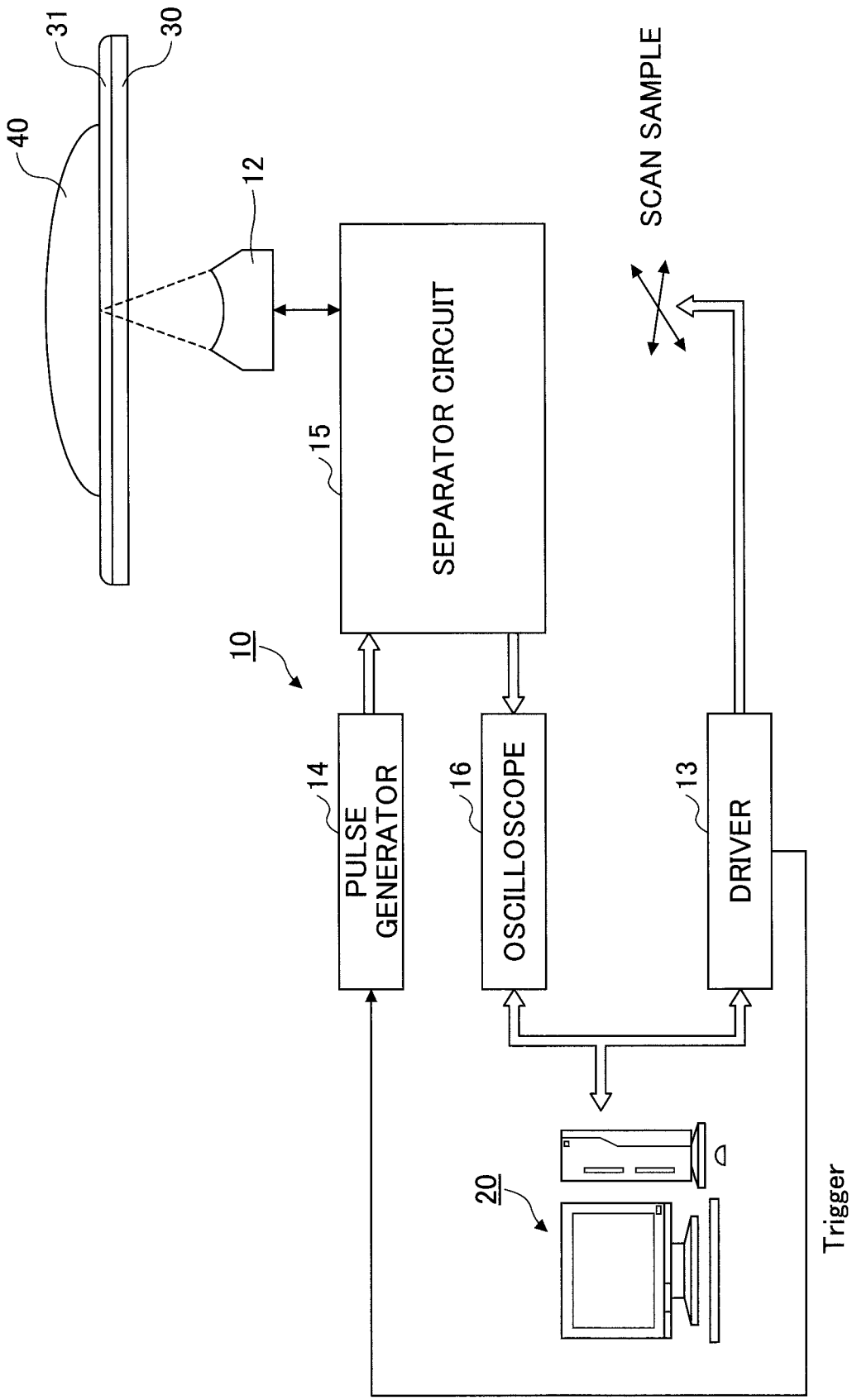
FIG. 1 is a schematic diagram illustrating ultrasonic measurement according to an embodiment.

FIG. 1 is a schematic diagram of ultrasonic measurement according to an embodiment. The ultrasonic measurement is performed using, for example, an ultrasonic measuring instrument 10 and a personal computer (PC) 20 for data analysis.

In this example, the ultrasonic measuring instrument 10 includes a pulse generator 14, an oscilloscope 16, a separator circuit 15 for separating transmitted and reflection acoustic waves, and the transducer 12. A drive pulse generated by the pulse generator 14 is input to the transducer 12. The transducer 12 converts the electric pulse signal into mechanical vibration to generate an ultrasonic wave, and irradiates the sample 40 with the ultrasonic wave. The acoustic wave reflected back from the sample 40 is detected by the transducer 12 and converted into an electric signal.

The transducer 12 is connected to the separator circuit 15 that is configured to separate a signal to be input to the transducer 12 and a reflected signal output from the transducer 12. The acoustic impedance of the reflected signal is measured by the oscilloscope 16. The measured waveform is input to the PC 20 and analyzed.

The PC 20 is an example of an information processing apparatus, which may be of any type such as a tablet device, a smartphone, or a notebook computer. The oscilloscope 16 is an example of a tool that measures a reflected wave. Any type of circuitry device may be used as the measuring tool as long as the device can receive a reflected wave and measure the voltage signal. In place of the oscilloscope 16, a receiver circuit capable of detection and digital conversion of a reflected signal may be used.

The driver 13 scans the sample 40 held on a stage by driving the stage relative to the transducer 12. Using a trigger signal from the driver 13, the scan timing of the sample 40 and the pulse output timing of the pulse generator 14 may be synchronized to each other.

The sample 40 is placed on a transparent plate 30 via a couplant 31 such as water or a gel. In an embodiment, the second derivative of the acoustic impedance of the sample 40 is used to determine the interface position or the thickness of the target layer in the sample 40.

The sample 40 includes multiple layers having different mechanical properties. For example, human skin is formed of a plurality of layers with different mechanical properties, and the outermost horny layer has an elastic modulus (e.g., Young's modulus) two digits greater than that of the adjacent layer (namely, the epithelial layer of the epidermis excluding the horny layer). By clearly detecting the transition from the rigid horny layer to the soft epithelial layer skin layer based upon the change in the acoustic characteristics, the position of the interface between the horny layer and the adjacent layer and the thickness of the horny layer can be determined accurately.

In the conventional skin elasticity measurement using an elasticity meter such as a "cute meter" (registered trademark), a time duration for applying a stress or a torque onto the skin is long, and the response time is also long. Because the applied stress reaches the dermis located deeper in the skin than the epidermis, the elastic information obtained by the elasticity meter contains a large quantity of dermis information.

In contrast, ultrasonic waves are reflected by an interface at which the density changes, and accordingly, the characteristics of the skin surface can be determined by measuring the reflected waves from the surface layer of the skin. Noninvasive measurement is carried out using an ultrasonic wave of 400 MHz or less.

Figure 2:
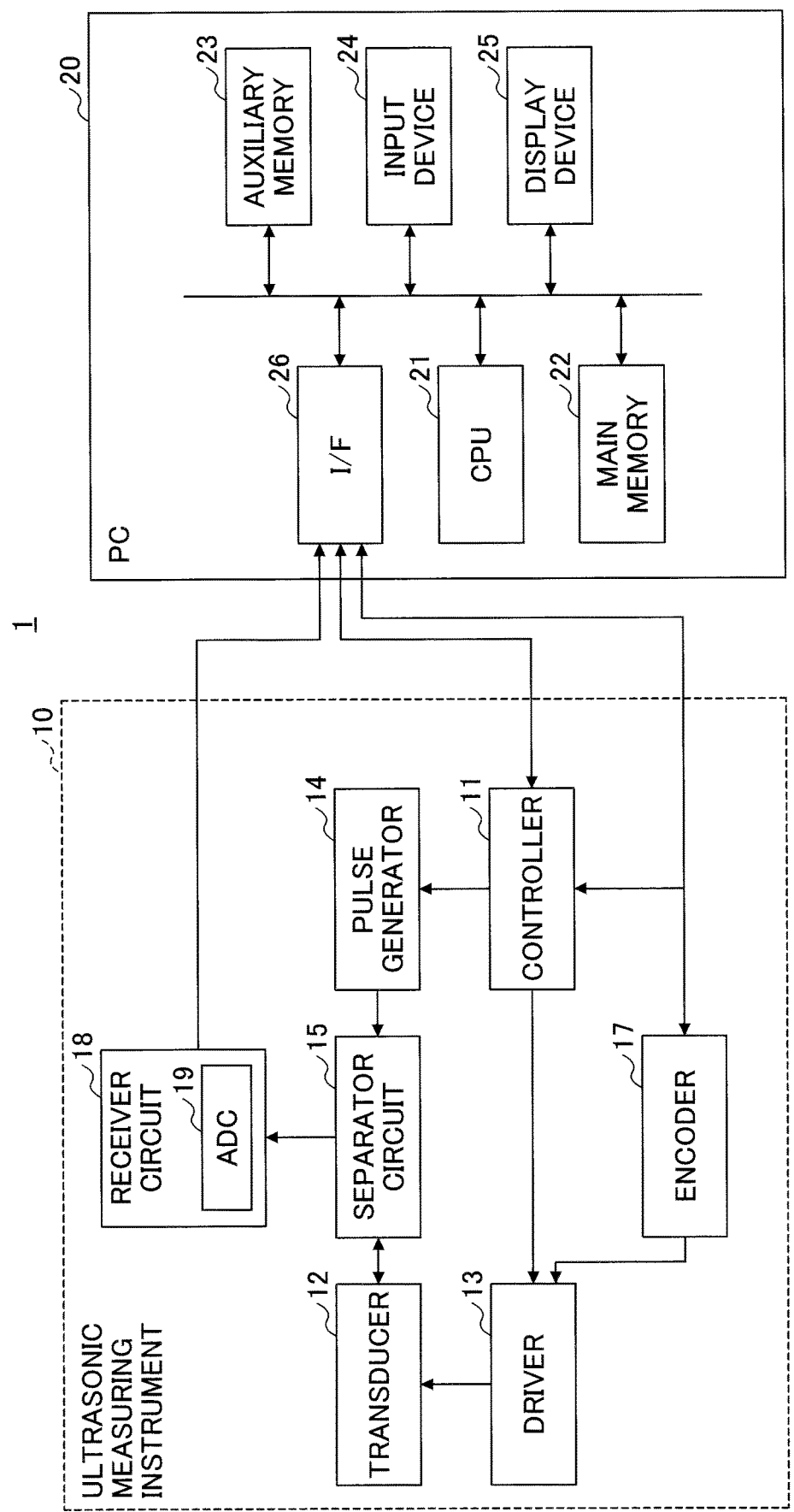
FIG. 2 is a block diagram of an ultrasonic measurement apparatus according to an embodiment.

FIG. 2 is a block diagram of an ultrasonic measurement apparatus 1 according to an embodiment. The ultrasonic measurement apparatus 1 includes an ultrasonic measuring instrument 10 and a PC 20. The ultrasonic measuring instrument 10 may be shaped in, for example, a probe as a whole, and it may have a window at the tip for inputting and outputting ultrasonic waves. The ultrasonic measuring instrument 10 may have a controller 11, a transducer 12, a driver 13, a pulse generator 14, an encoder 17, and a receiver circuit 18.

The controller 11 includes, for example, a memory and a microprocessor, and is configured to control the entire operation of the ultrasonic measuring instrument 10. The encoder 17 detects the coordinates of the stage on which the sample 40 is held.

The controller 11 controls the operations of the driver 13 based upon the coordinate information from the encoder 17. The controller 11 also controls the pulse generating timing of the pulse generator 14 in synchronization with the operation of the driver 13.

The electric pulse output from the pulse generator 14 is supplied to the transducer 12 by the separation circuit 15. The electric pulse is converted into an ultrasonic wave by the transducer 12, and the ultrasonic wave is incident on the sample 40. The transducer 12 converts a return wave reflected from the sample 40 into an electric signal. The reflected signal is supplied to the receiver circuit 18 via the separator circuit 15. The receiver circuit 18 detects and outputs the analog electric signal to an analog-to-digital converter (ADC) 19 at which the analog electric signal is converted to a digital signal. The digital signal is output from the ultrasonic measuring instrument 10 to the PC 20.

The ultrasonic measuring instrument 10 may be connected to the PC 20 by a connector cable such as a high-speed serial bus standard, or it may be wirelessly connected by a short-range wireless communication standard.

The PC 20 has a CPU 21, a main memory 22, an auxiliary memory 23, an input device 24, a display device 25, and an interface (I/F) 26. The measurement result acquired by the ultrasonic measuring instrument 10 is input to the CPU 21 via the interface 26 and analyzed by the CPU 21.

The main memory 22 is a primary memory space including a read only memory (ROM) and a random access memory (RAM). The ROM stores calculation parameters, programs, or the like necessary for ultrasonic measurement and analysis. The RAM is used as a work area for ultrasonic analysis. The auxiliary memory 23 may be a solid state drive (SSD), a hard disk drive (HDD), or the like, and it performs long-term storage of programs, data, parameters, or the like.

The input device 24 includes an input user interface such as a touch panel, a mouse, or a keyboard. The display device 25 is a monitor display such as a liquid crystal display, a plasma display, or an organic electroluminescence (EL) display. When the ultrasonic measurement program is installed, the CPU 21 reads the ultrasonic measurement program from the main memory 22 or the auxiliary memory 23, analyzes the reflection signal, constructs image data, and displays the image of the skin structure on the display device 25.

Figure 3:
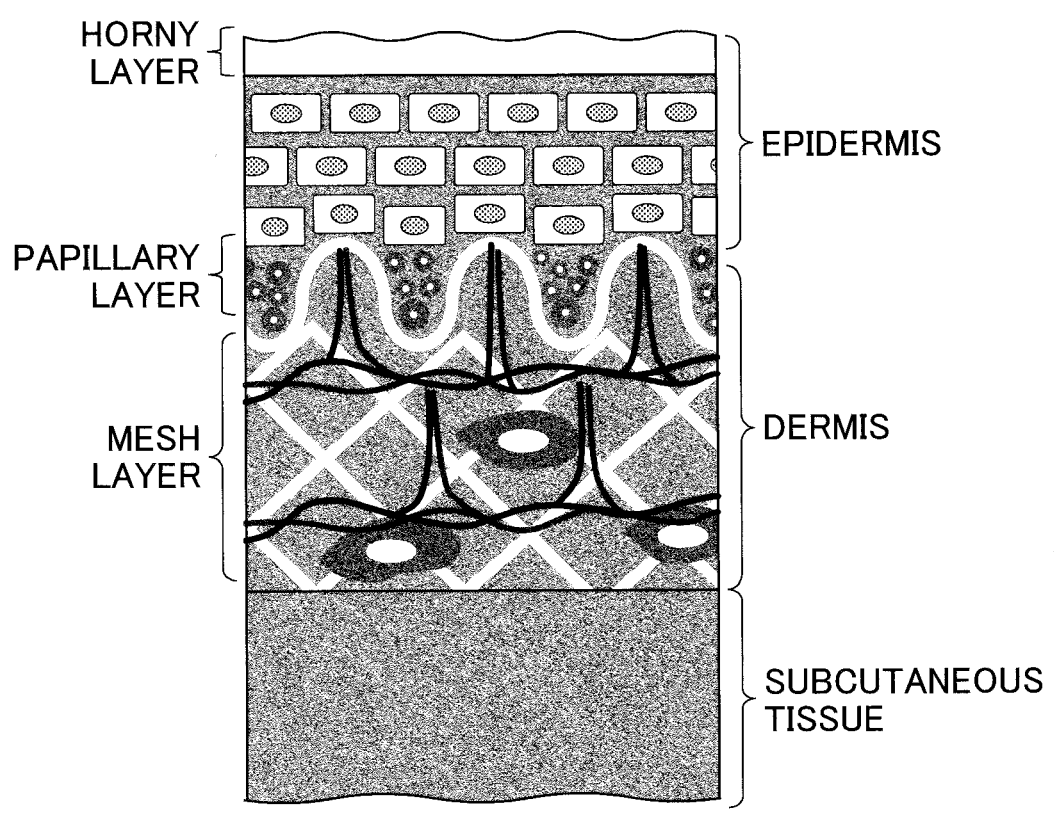
FIG. 3 illustrates a cross-sectional structure of human skin which is an example of a measurement target.

FIG. 3 illustrates a cross-sectional structure of human skin which is an example of the object to be measured. Skin includes epidermis including the outermost horny layer, and the dermis beneath the epidermis. Beneath the dermis is subcutaneous tissue. The horny layer has a barrier function that prevents evaporation of water from the body and avoids intrusion of foreign matters from the outside. The dermis occupies about 95% of the skin and is the structural foundation of the skin. The dermis includes a papillary layer and a mesh layer. The dermis keeps the skin elastic and acts as a cushion against external pressure and destructive forces.

If evaluation of changes in the mechanical properties of not only the horny layer, but also the epithelial layer that is immediately beneath the horny layer, and the dermis is achieved, then new skincare value will be provided. It is useful to allow evaluation of the individual layers of a multilayer structure containing lamination of thin films such as resin films and polymer gel films, as well as skin or biological membranes.

Figure 4:
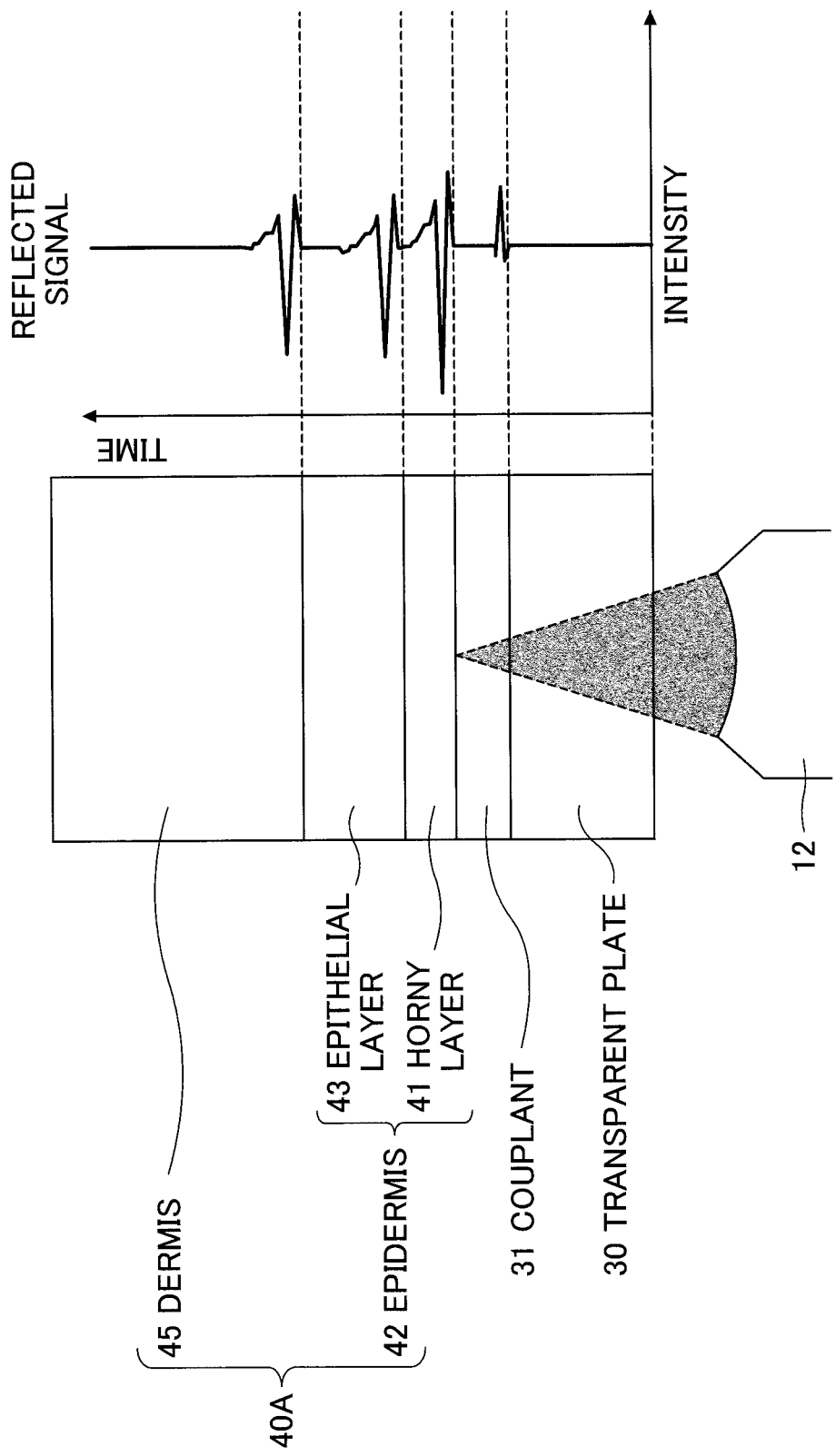
FIG. 4 illustrates a reflected signal obtained by ultrasonic measurement.

FIG. 4 illustrates a reflected signal acquired from ultrasonic measurement. The sample 40A is a surface layer of a human skin collected by an adhesive tape or the like. The sample includes an epidermis 42 including the outermost horny layer 41, and dermis 45. A layer other than the horny layer 41 in the epidermis 42 may be referred to as an epithelial layer 43.

The sample 40A is placed on the transparent plate 30 via a couplant 31 such as water or a gel. The transparent plate 30 is a plastic plate made of, for example, an acrylic resin.

A wave reflected from the sample 40A may contain a component reflected back from the subcutaneous tissue deeper than the dermis. In the embodiment, only the reflection signals from the target layers are extracted using a time window. Here, reflection signals obtained from the individual layers starting from the transparent plate up to the dermis are extracted to acquire distribution of acoustic impedance.

Acoustic impedance (Z) indicates extent of difficulty of transmission of an ultrasonic wave through a material, and it is expressed as $$Z = p/v = \rho * C$$

Where p denotes the sound pressure (Pa), v denotes the volume velocity (m³/s), ρ denotes the density of the object to be measured (kg/m³), and C denotes the sound velocity (m/s) unique to the substance. Because the densities of the individual layers forming the skin and sound velocities unique to the individual layers are different, the acoustic impedance also varies among the layers. The greater the difference in acoustic impedance between the adjacent layers forming the skin, the stronger the reflection.

Calculation of the acoustic impedance from the reflected and received signal is performed by the CPU 21 based upon, for example, a time domain reflection (TDR) method.

The ultrasonic pulse incident on the sample is reflected by impedance mismatch. The reflection coefficient R is expressed by Equation (1).

$$R = \frac{\text{(reflected signal voltage)}}{\text{(incident signal voltage)}} = \frac{Z_L - Z_O}{Z_L + Z_O} \quad (1)$$

where $Z_L$ denotes the impedance of the sample 40A, and $Z_O$ denotes a known impedance. In the embodiment, the impedance of the couplant 31 is used as the known impedance.

The impedance of the sample 40A is expressed by Equation (2).

$$Z_L = \frac{1+R}{1-R} Z_O \quad (2)$$

Based upon the value of R, $Z_L$ is determined. The value of R is obtained by dividing the reflected signal voltage at each position in the depth direction by the input pulse voltage. When the positions of reflection vary, changes in impedance are observed at different time positions along the time axis.

Figure 5:
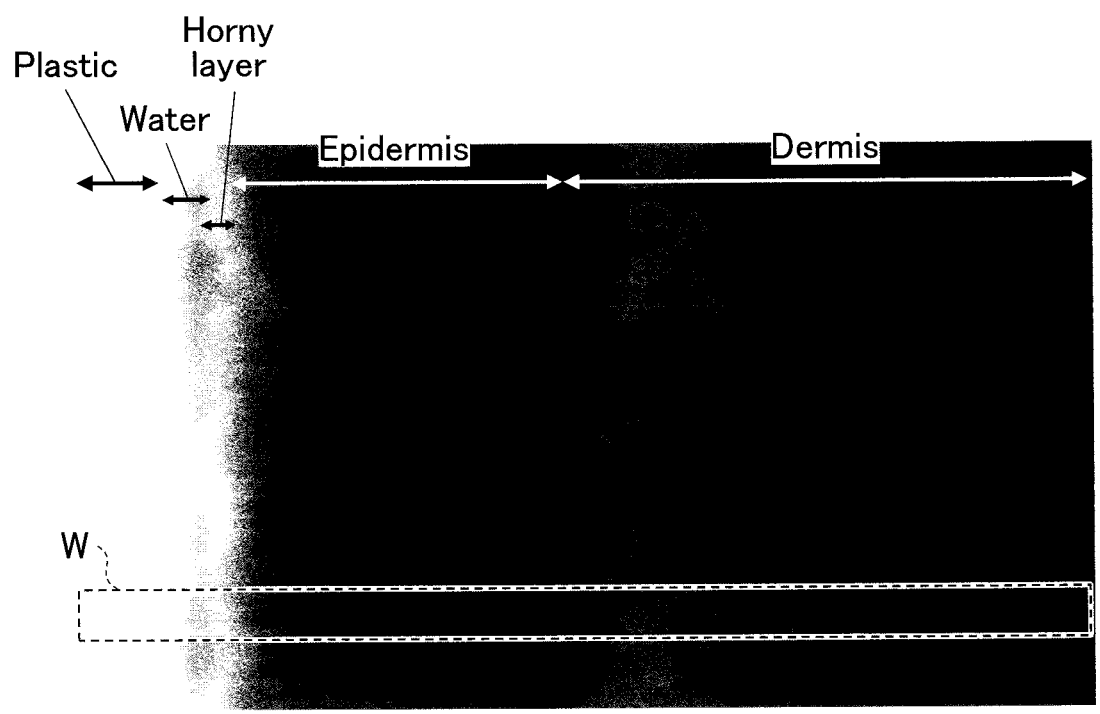
FIG. 5 illustrates a distribution of calculated acoustic impedances.

FIG. 5 illustrates distribution of the calculated acoustic impedances in the depth direction, using a transducer 12 with a center frequency of 80 MHz. The region W surrounded by the dashed line is analyzed from the reflection signals acquired within a predetermined time window among those signals received from the sample 40A. The region W extends to the depth direction starting from plastic, through water, horny layer, epithelial layer, and reaching dermis. In the figure, the brighter area represents higher acoustic impedance (MNs/m³).

Figure 6:
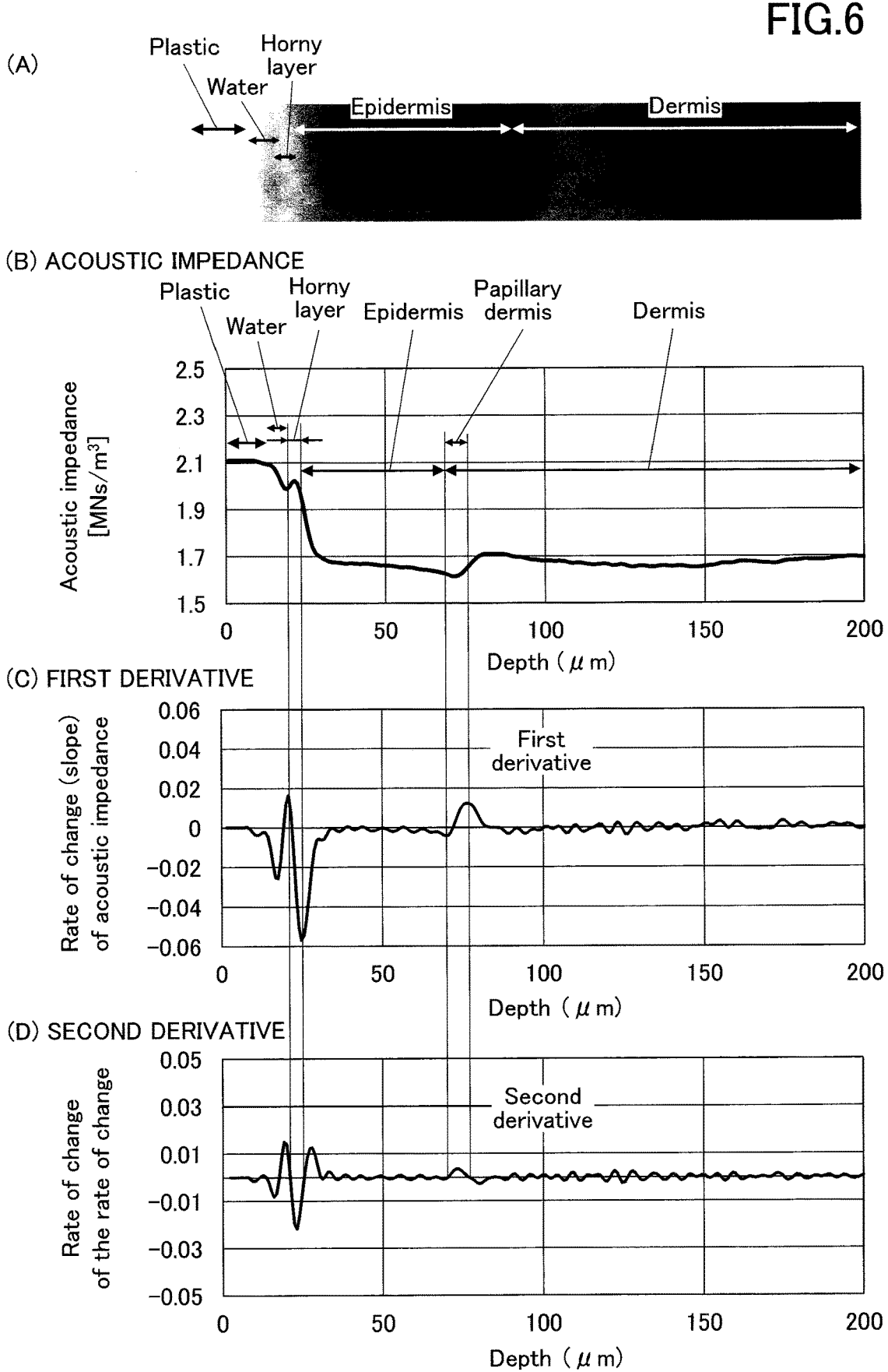
FIG. 6 illustrates the relation between acoustic impedance and the first derivative and the second derivative.

FIG. 6 illustrates the relation between the acoustic impedance and the first and the second derivatives thereof. In FIG. 6, chart (A) indicates the distribution of the acoustic impedance along the depth direction, chart (B) illustrates the acoustic impedance calculated from the reflected signal, chart (C) illustrates the first derivative of the acoustic impedance, and chart (D) illustrates the second derivative of the acoustic impedance. The horizontal axes of the charts (B), (C), and (D) represent depth positions (μm) which correspond to the positions in the depth direction of chart (A).

In chart (A) of FIG. 6, the acoustic impedance of the transparent plate 30 made of plastic is high, indicated as a bright area, while the acoustic impedance of water serving as the couplant 31 is low. The acoustic impedance of the horny layer is different from that of water; however, it is difficult to definitely identify the interfaces of the horny layer, where begins and where ends. Similarly, it is difficult to identify the interface between the epidermis and the papillary layer of the dermis and the interface between the papillary layer and the next layer of the dermis.

The first derivative represents the rate of change of the acoustic impedance. When the absolute value of the rate of change is large in the first derivative, it means that the acoustic impedance changes greatly. It may be inferred that the interface is located at a position where the magnitude of the rate of change is large; however, it is still difficult to accurately identify the positions of the interfaces of the individual layers.

The second derivative represents a rate of change of the rate of change, namely, the sign or the direction of the curvature of the rate of change, depending on whether the curvature indicates a positive change (i.e., downward convex) or a negative change (i.e., upward convex). A second derivative with its magnitude zero means that the profile of the curvature of the rate of change switches from a downward convex to an upward convex change, or from an upward convex to a downward convex. The point at which the sign of the curvature of the rate of change is reversed is called an "inflection point".

In the embodiment, an inflection point at which the second derivative of the acoustic impedance becomes zero is specified as a position of interface, and the distance between an inflection point to the next inflection point is determined as the thickness of the layer. It has to be considered that, a small change in the acoustic impedance due to variation in the density within the same layer or fluctuation of measurement is also reflected when calculating the rate of change by the first-order differentiation, and that the sign of the curvature of the second derivative is often flipped in short steps. So, very small changes less than a predetermined level in the second derivatives are regarded as being irrelevant to an acoustic impedance change at an interface between different layers.

In the examples of FIG. 6, inflection point at which the sign of the curvature of the rate of change flips from positive (plus) to negative (minus) is the entrance of the horny layer. In the region deeper than the entrance of the horny layer, the area where the slope of the rate of change is maintained negative is inside the horny layer. A zero point at which the sign of the curvature of the rate of change flips to positive is the interface between the horny layer and the epithelial layer. By specifying an inflection point (or a zero point of the second derivative) at which the sign of the curvature of the rate of change is flipped, a position of the interface of the horny layer can be specified accurately.

Calculation of the second derivatives and identification of inflection points can be performed by the CPU 21 of the PC 20 using, for example, a second derivative filtering method.

Because in this measurement the couplant 31 is interposed between the transparent plate 30 and the skin sample 40A, the first inflection point appearing in the depth direction of skin after the variation in the rate of change exceeds a predetermined level and at which the curvature of the rate of change flips from positive to negative is determined as the beginning of the horny layer. The next zero point (inflection point) in the depth direction at which the curvature of the rate of change flips from negative to positive is defined as the end of the horny layer. The distance between the first inflection point and the next inflection point is determined as the thickness of the horny layer.

Similarly, for the papillary dermis, a point at which the variation in the rate of change first exceeds the predetermined threshold level in the region a predetermined amount deeper than the horny layer is specified, and the zero points located both sides of the corresponding peak of the second derivative are specified as the interfaces. The distance between these two zero points is determined as the thickness of the papillary layer. The range from the end position of the horny layer to the start position of the papillary layer may be determined as the thickness of the epithelial layer excluding the horny layer.

Figure 7:
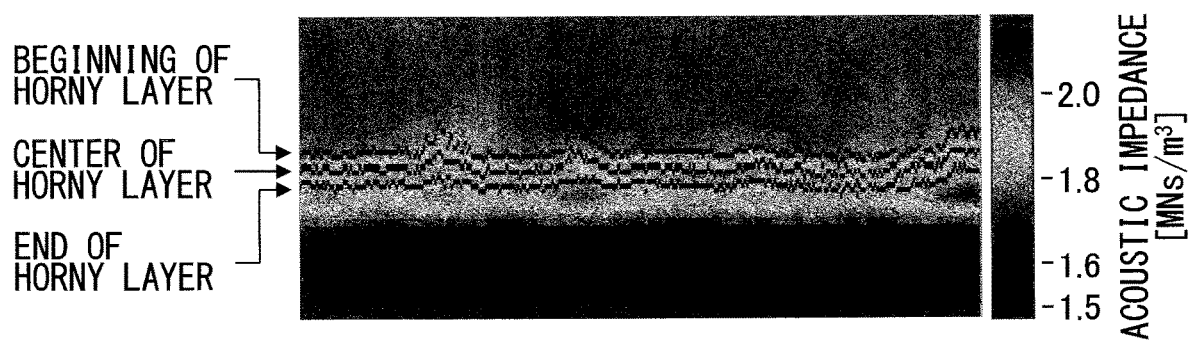
FIG. 7 is a cross-sectional image of a horny layer identified by the method of FIG. 6.

FIG. 7 is a cross-sectional view of the horny layer obtained by scanning the ultrasonic wave one-dimensionally over the sample 40A and identifying the horny layer by the method of FIG. 6. The vertical axis represents the depth of the skin, and a horizontal position corresponds to the position in the one-dimensional scanning. The center of the horny layer is acquired by plotting the midpoint between the first inflection point and the next inflection point that appear after the change in the rate of change exceeds the predetermined threshold level. The roughness of the skin surface can be observed, together with the thickness of the horny layer.

From the measurement results of FIG. 6 and FIG. 7, it is understood that the skin condition can be evaluated by measuring the thickness of the horny layer noninvasively using ultrasonic waves. For example, the thickness of the horny layer correlates to the average acoustic impedance at the center of the horny layer.

Figure 8:
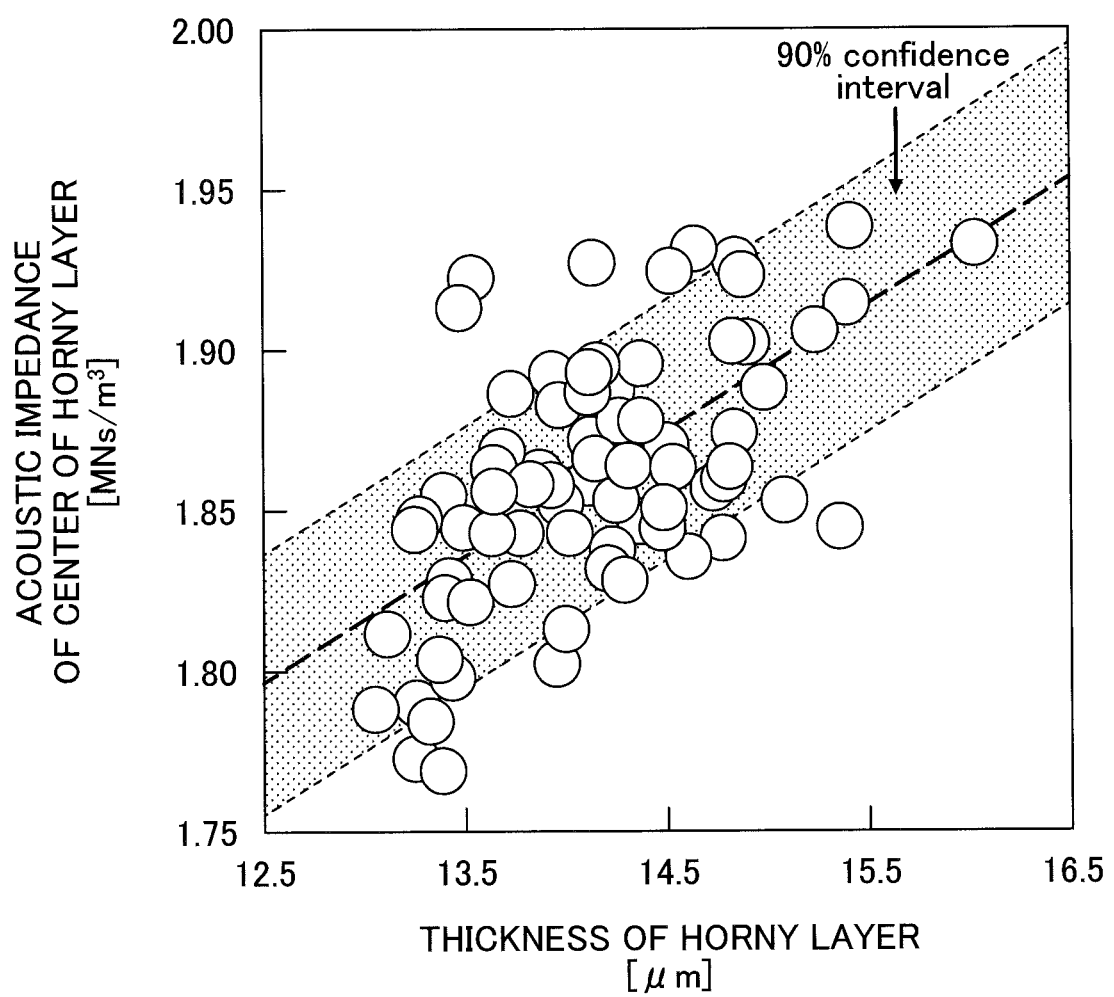
FIG. 8 illustrates the relation between horny layer thickness and average acoustic impedance at the center of horny layer.

FIG. 8 is a diagram illustrating the relation between the thickness of the horny layer and the average acoustic impedance at the center of the horny layer. From thirty three (33) persons ranging in age from their twenties to sixties, acoustic impedance images were obtained, collecting data from three different locations on the cheek per person. The thickness ($\mu$m) of the horny layer and the acoustic impedance at the center of the horny layer were determined by the above-described second-order differentiation method.

Most of the data fall within the 90% confidence interval, indicating that the thickness of horny layer and acoustic impedance are correlated. As the thickness of horny layer increases, the acoustic impedance at the center of horny layer also increases. This indicates that when the horny layer becomes thicker, the skin loses its flexibility and becomes tough.

Figure 9:
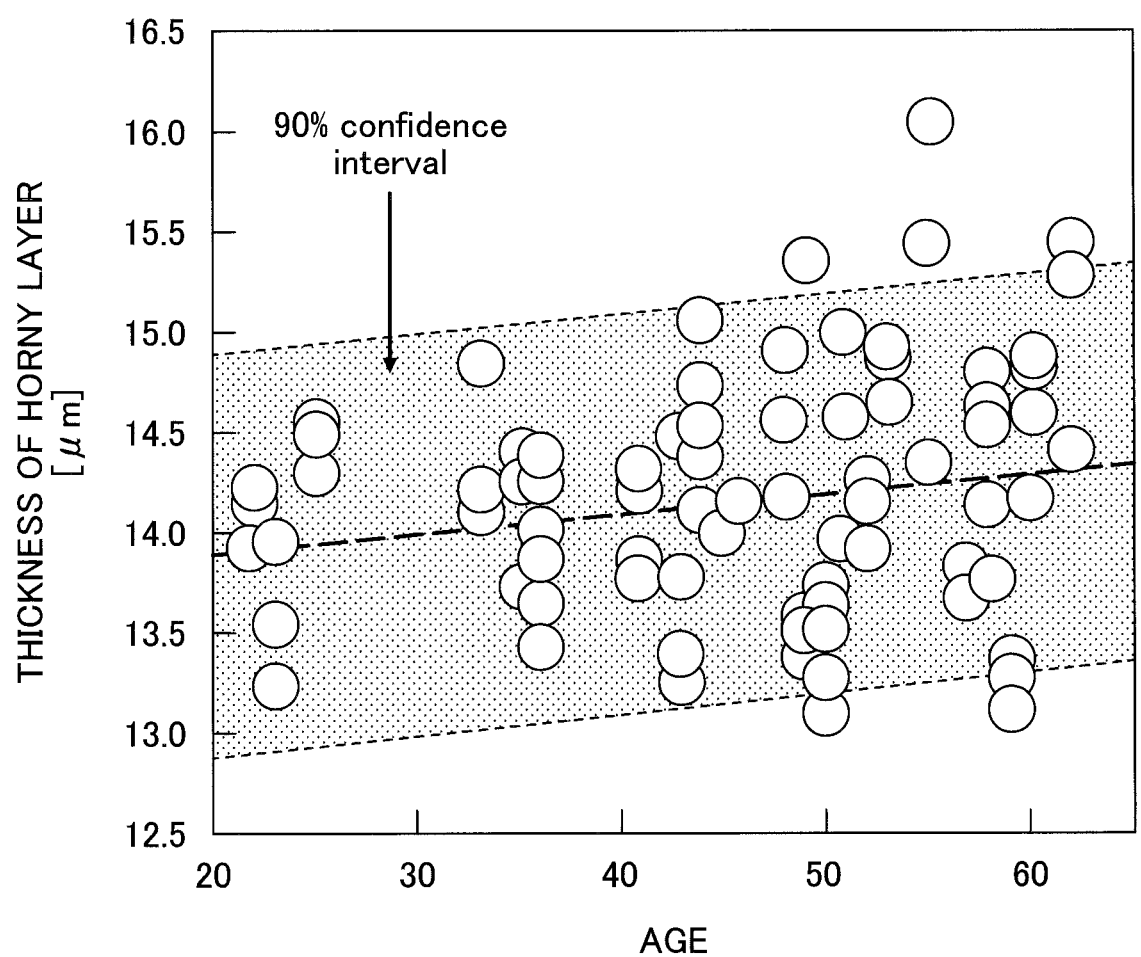
FIG. 9 plots horny layer thickness as a function of age.

FIG. 9 is a diagram plotting the thickness of horny layer as a function of age based upon the acoustic impedance images obtained from the same group of subjects. Again, most of the data fall within the 90% confidence interval, and it can be seen that the age and the thickness of horny layer linearly correlate each other. As we age, the horny layer becomes thicker and the skin loses softness.

Compared to the fact that age-related changes in the cheeks cannot be derived from the water profile obtained by conventional Raman confocal microscopy, the configuration and process of the embodiment is advantageous because age-related change in cheeks can be measured by performing simple differential analysis on the ultrasonic echo signals.

Figure 10A:
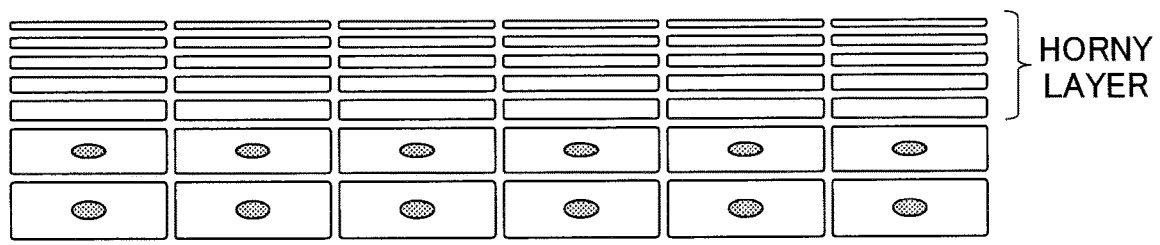
FIG. 10A schematically illustrates a change in skin condition.
Figure 10B:
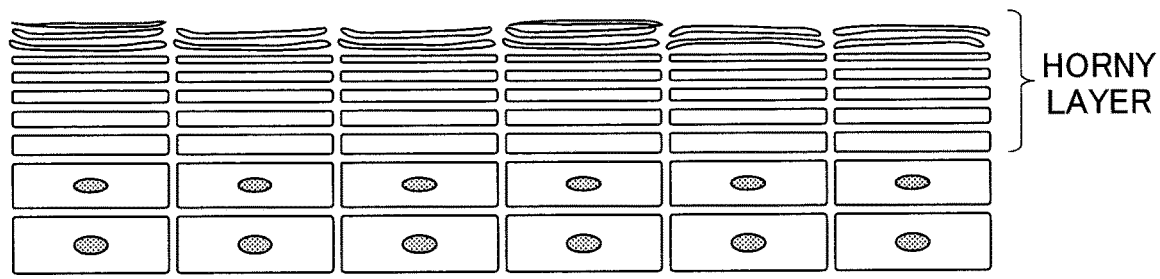
FIG. 10B schematically illustrates a change in skin condition.

FIG. 10A and FIG. 10B schematically illustrate a change in skin condition based upon the results of FIG. 8 and FIG. 9. FIG. 10A illustrates normal skin. Skin cells are pushed out from the base of the epidermis (i.e., the interface between the epidermis and the papillary layer in FIG. 3) toward the top surface of the skin in about two weeks, and become horny cells. The horny cells are excreted as dead skin from the surface of the skin for about two weeks. This cycle is called turnover. When the turnover cycle is disturbed, the old horny layer remains on the skin and the horny layer becomes thicker as illustrated in FIG. 10B. The old horny layer remaining on the skin becomes denser and the acoustic impedance level rises.

From the discussion above, the acoustic impedance of normal skin is measured in advance for each age to collect data of average thickness of horny layer, and the collected data are stored in the memory 22 of the PC 20. By comparing the acoustic impedance value or the thickness of the horny layer measured from a monitored person with the normal average value stored in the memory 22, the current skin condition of the monitored person can be evaluated.

The above-described ultrasonic measurement and thickness measurement of a layer can be applied not only to measurement of skin but also to measurement of a multi-layer structure with lamination of thin films.

Figure 11:
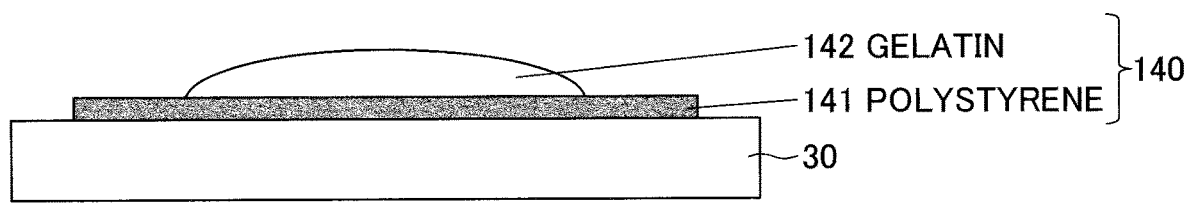
FIG. 11 is a schematic diagram of a model of a multilayer structure to which ultrasonic measurement is applied.

FIG. 11 is a schematic diagram of a multilayer model to which the ultrasonic measurement of the embodiment is applied. As an example of the multilayer model, a two-layer model 140 of polystyrene 141 and gelatin 142 placed on the transparent plate 30 is used. The two-layer model 140 is irradiated with ultrasonic waves, and a distribution of the acoustic impedance in the depth direction is calculated from the reflected signals. From the second derivative of the acoustic impedance, inflection points are identified, whereby the positions of the interfaces can be specified. The thickness of the target layer can be determined from the distance between the inflection points.

Figure 12:
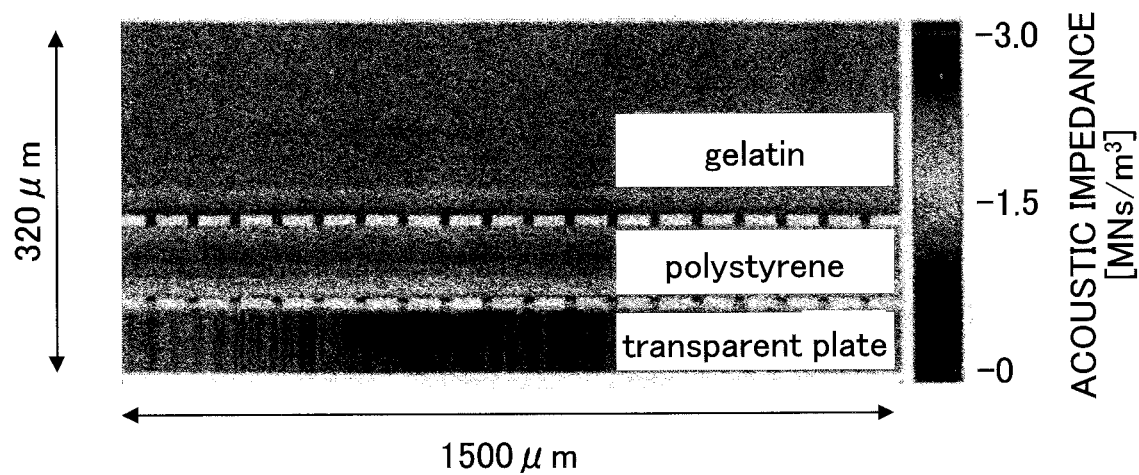
FIG. 12 is an image representing distribution of acoustic impedance in the depth direction measured from the model of FIG. 11.

FIG. 12 illustrates a distribution of the acoustic impedance in the depth direction of the two-layer model 140 of FIG. 11. The acoustic impedance varies depending on the materials of the layers constituting the multilayer structure, and thus, the layered structure can be specified to a certain degree. In this example, the acoustic impedance of the transparent plastic plate is relatively high and the acoustic impedance of the two-layer structure of polystyrene 141 and gelatin 142 is low, bordering at 1.5 MNs/m$^3$. In the two-layer structure, the acoustic impedance of polystyrene 141 is as low as that of water, and the acoustic impedance of gelatin 142 is higher.

The change in the acoustic impedance along the depth of the two-layer model 140 exhibits the same tendency as one illustrated in chart (B) of FIG. 6, in which the acoustic impedance varies according to the layers of plastic, water, and horny layer. By performing second-order differentiation on the acoustic impedance measured in FIG. 12, a depth-direction profile similar to that of chart (D) of FIG. 6 is obtained. The first inflection point that appears after the change in the rate of change exceeds the predetermined threshold level and at which the curvature of the rate of change flips from positive to negative, represents the interface between polystyrene 141 and gelatin 142. The distance from this inflection point to the next inflection point at which the curvature of the rate of change flips from negative to positive is the thickness of the gelatin 142.

In this manner, the ultrasonic measurement of the embodiment is applicable not only to skin diagnosis but also to measurement of a multilayer structure with multiple thin films laminated.

Figure 13:
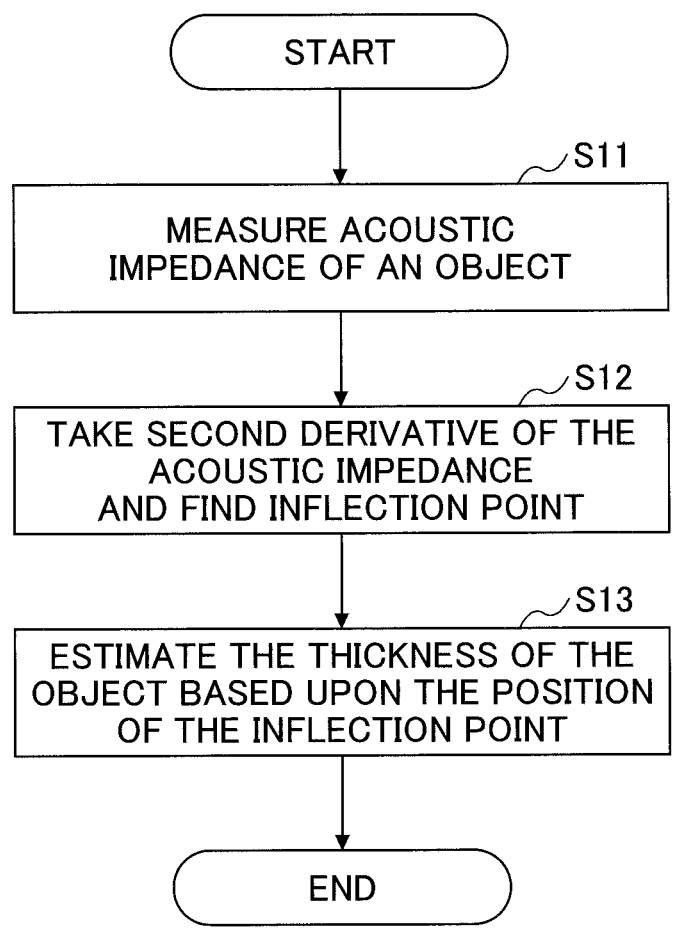
FIG. 13 is a flowchart of an ultrasonic measurement method according to an embodiment.

FIG. 13 is a flowchart of ultrasonic measurement method according to the embodiment. First, acoustic impedance is measured in the depth direction of an object to be measured (S11). To be more precise, the object is irradiated with ultrasonic waves and return waves reflected from the object are received. The acoustic impedance can be calculated from equation (2). As a reference substance that has a known acoustic impedance $Z_0$, a known couplant such as water or a gel may be used.

Next, second-order differentiation is performed on the acoustic impedance and inflection points (i.e., zero points in the second derivative) are specified (S12). The second-order differentiation and the identification of the inflection points may be performed by a differential filtering process of the CPU 21, as described above. From the positions of the inflection points, the thickness of the target layer of the monitored object can be estimated and output (S13).

This method allows the interface position and the thickness of a very thin film to be determined accurately by a simple process.

FIG. 14 is a flowchart of skin evaluation using ultrasonic measurement according to the embodiment. First, the acoustic impedance in the depth direction of a skin sample is measured (S21). The skin sample may be obtained by peeling the epidermis of the skin with an adhesive tape or the like. The skin sample is irradiated by ultrasonic waves and acoustic impedance is calculated from the reflected waves returned from the skin sample.

Then, second-order differentiation is performed on the acoustic impedance and inflection points are specified (S22). Then the thickness of the horny layer is determined from the positions of the inflection points (S23). Based upon the thickness of the horny layer, skin parameters such as elasticity or stiffness of skin, skin age, etc. are evaluated (S24). Information about elasticity and skin age of average normal skin may be stored in advance in the memory 22, associated with the thickness of the horny layer. Evaluation results may be output based upon comparison between the measurement result and the pre-stored information.

With this method, skin condition can be evaluated appropriately with a simple technique.

The present invention has been described above based upon specific examples. However, the present invention is not limited to the above-described examples, but includes various modifications and alterations. For example, the acoustic impedance and/or the thickness of the measured object obtained from the second derivative of the acoustic impedance may be converted into other mechanical characteristics such as a bulk modulus or a water content. Thereby, the mechanical properties of skin or another thin film can be determined quickly by ultrasonic measurement.

The cross-sectional view of the horny layer may be displayed as an image such that the roughness of the skin surface can be visually recognized. A two-dimensional distribution image of the acoustic impedance may be displayed such that the uniformity of the smoothness of the skin surface can be visually understood.

The two-dimensional distribution image of the acoustic impedance may be generated by the CPU 21 of the PC 20. A predetermined area of a skin sample may be scanned relative to an ultrasonic wave to receive reflected waves and calculate a two-dimensional distribution of acoustic impedance. Image data may be generated and displayed by mapping the acoustic impedance of each coordinate (i.e., pixel position) to a gradation or a color value.

Instead of collecting a skin sample using an adhesive tape, a probe-type ultrasonic measuring instrument may be used to directly irradiate the measurement site of the object with ultrasonic waves and calculate the acoustic impedance. In this case, a couplant such as saline or gel may be applied directly onto the measurement site of the object. By pressing the plastic plate of an ultrasonic wave irradiation window against the measurement site of the object via the couplant, the same measuring condition as that illustrated in FIG. 4 is created.

When achieving the ultrasonic measurement method of the embodiment by an ultrasonic measurement program installed in the PC 20, the ultrasonic measurement program stored in the main memory 22 or the auxiliary memory 23 is read out and executed by the CPU 31. The ultrasonic measurement program causes the CPU 31 to execute the procedures of acquiring a reflection signal of an ultrasonic waves reflected from an object to be measured, calculating an acoustic impedance in a depth direction of the object from the reflection signal, estimating a thickness of the object based upon an inflection point determined by a second derivative of the acoustic impedance, and outputting an estimation value of the thickness.

What is claimed is:

1. An ultrasonic measurement method comprising:
irradiating an object to be measured with an ultrasonic wave;
acquiring a reflection wave from the object,
calculating at a processor an acoustic impedance in a depth direction of the object from the reflection wave; and
estimating and outputting a thickness of the object based upon an inflection point determined by second-order differentiation of the acoustic impedance.

2. The ultrasonic measurement method as claimed in claim 1,
wherein the object to be measured is an outermost layer of a multilayer structure, and
wherein a distance from a first inflection point that first exceeds a predetermined threshold level in the depth direction to a next inflection point located deeper than the first inflection point and at which a sign of a curvature of a rate of change of the acoustic impedance is flipped from negative to positive, is output as the thickness.

3. The ultrasonic measurement method as claimed in claim 2,
wherein the first inflection point and the next inflection point are determined by a second-order differentiation filtering process.

4. The ultrasonic measurement method as claimed in claim 1, further comprising:
outputting an evaluation value of stiffness or elasticity of the object based upon at least one of the thickness and a calculation value of the acoustic impedance.

5. The ultrasonic measurement method as claimed in claim 1, further comprising:
generating and outputting an image representing a characteristic of the object to be measured based upon a distribution of the acoustic impedance in the depth direction.

6. The ultrasonic measurement method as claimed in claim 1,
wherein the object to be measured is a biological membrane.

7. The ultrasonic measurement method as claimed in claim 1,
wherein the object to be measured is human skin, and an estimation value of a skin age is output based upon the thickness.

8. A program storage device readable by a machine comprising:
a memory that stores an ultrasonic measurement program, the ultrasonic measurement program causing the machine to execute procedures of
acquiring a reflection signal of an ultrasonic wave reflected from an object to be measured;
calculating an acoustic impedance in a depth direction of the object from the reflection signal;
estimating a thickness of the object based upon an inflection point determined by a second derivative of the acoustic impedance; and
outputting an estimation value of the thickness.

9. An ultrasonic measurement apparatus: comprising:
an ultrasonic measuring instrument configured to irradiate an object to be measured with an ultrasonic wave and receive a reflection wave from the object; and
a processor that calculates an acoustic impedance in a depth direction of the object based upon the reflection wave, and outputs an estimation value of a thickness of the object based upon an inflection point determined from a second derivative of the acoustic impedance.

10. The ultrasonic measurement apparatus as claimed in claim 9,
wherein the processor outputs an evaluation value of stiffness or elasticity of the object based upon at least one of the thickness and a calculation value of the acoustic impedance.

11. The ultrasonic measurement apparatus as claimed in claim 9, further comprising:
a display device,
wherein the processor generates an image representing a characteristic of the object to be measured based upon a distribution of the acoustic impedance in the depth direction, and
the display device displays the image generated by the processor.

* * * * *